(12) United States Patent
Morsell

(10) Patent No.: US 11,337,490 B2
(45) Date of Patent: May 24, 2022

(54) FOOT PAIN RELIEF DEVICE

(71) Applicant: Warfield T Morsell, Phoenix, AZ (US)

(72) Inventor: Warfield T Morsell, Phoenix, AZ (US)

( * ) Notice: Subject to any disclaimer, the term of this patent is extended or adjusted under 35 U.S.C. 154(b) by 267 days.

(21) Appl. No.: 16/808,507

(22) Filed: Mar. 4, 2020

(65) Prior Publication Data

US 2021/0274886 A1    Sep. 9, 2021

(51) Int. Cl.
*A43B 17/18* (2006.01)

(52) U.S. Cl.
CPC .................... *A43B 17/18* (2013.01)

(58) Field of Classification Search
CPC ....... A43B 7/148; A43B 7/149; A43B 7/1415; A43B 7/1485; A43B 17/18; A43B 17/026; A43B 17/02; A43B 13/188; A43B 19/00
See application file for complete search history.

(56) References Cited

U.S. PATENT DOCUMENTS

| | | | |
|---|---|---|---|
| 5,329,705 A * | 7/1994 | Grim | A43B 17/026 36/88 |
| 5,761,834 A * | 6/1998 | Grim | A43B 17/035 36/88 |
| 6,792,699 B2 * | 9/2004 | Long | A43B 1/0081 36/88 |
| 8,813,391 B1 * | 8/2014 | Khaitan | A43B 7/1425 36/44 |
| 2007/0079532 A1 * | 4/2007 | Ramirez | A43B 7/144 36/140 |
| 2007/0107261 A1 * | 5/2007 | Cheskin | A43B 17/02 36/44 |
| 2007/0294922 A1 * | 12/2007 | Ma | A43B 7/144 36/142 |
| 2012/0246971 A1 * | 10/2012 | Donzis | A43B 7/149 36/43 |
| 2013/0104419 A1 * | 5/2013 | Horesh | A43B 7/149 36/43 |
| 2016/0021972 A1 * | 1/2016 | Grelle | A43B 17/02 36/140 |

* cited by examiner

*Primary Examiner* — Jila M Mohandesi
(74) *Attorney, Agent, or Firm* — Bruce A. Lev

(57) ABSTRACT

A foot pain relief device formed as a shoe or boot insert comprising a plurality of removable pieces designed to be selectively removed from the insert to thereby create a hollow portion, indentation, dip, concavity, groove, or impression area of the insert that allows the injured area to be free from impact of any sort while going through its healing process while the user continues daily activities without feeling discomfort or pain from the injured area of the foot.

9 Claims, 3 Drawing Sheets

US 11,337,490 B2

FOOT PAIN RELIEF DEVICE

CROSS-REFERENCE TO RELATED APPLICATION

There are no related applications incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

1. Field of the Invention

This invention relates generally to foot cushions, shoe inner soles, shoe inserts and orthotics. Use of the invention is to provide relief for the user's foot where there is an injured area to the bottom of the foot.

2. Description of the Related Art

There is no immediate solution to provide protection for a user's damaged foot (bottom of the foot area) to be completely free from impact or shock when a user places his or her foot in a shoe or boot. Existing foot relief products use gel, rubber layers, soft materials, and other types of materials to provide comfort to a user's damaged foot (i.e., plantar fasciitis). However, when any of these prior products are used the damaged area of the foot still makes contact with a surface creating some type of shock at impact and a degree of some discomfort or pain for the user.

Accordingly, the present invention overcomes these disadvantages associated with the prior art by removing sections of the device correlating to where the foot is damaged thereby creating a hollow indentation, dip, concavity, groove, or impression area allowing the injured area to be free from impact of any sort while going through its healing process while the user continues daily activities without feeling discomfort or pain from the injured area of the foot.

BRIEF SUMMARY OF THE INVENTION

In view of the foregoing disadvantages inherent in the prior art, the present invention provides a foot pain relief device formed as a shoe or boot insert comprising a plurality of removable pieces designed to be selectively removed from the insert to thereby create a hollow portion, indentation, dip, concavity, groove, or impression area of the insert that allows the injured area to be free from impact of any sort while going through its healing process while the user continues daily activities without feeling discomfort or pain from the injured area of the foot.

There has thus been outlined, rather broadly, the more important features of the invention in order that the detailed description thereof that follows may be better understood and in order that the present contribution to the art may be better appreciated.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. The invention is capable of other embodiments and of being practiced and carried out in various ways. Also, it is to be understood that the phraseology and terminology employed herein are for the purpose of descriptions and should not be regarded as limiting.

BRIEF DESCRIPTION OF THE DRAWINGS

The figures which accompany the written portion of this specification illustrate embodiments according to the teachings of the present invention.

The various embodiments of the present invention will hereinafter be described in conjunction with the appended drawings.

DETAILED DESCRIPTION

The embodiments of the present disclosure described below are not intended to be exhaustive or to limit the disclosure to the precise forms disclosed in the following detailed description. Rather, the embodiments are chosen and described so that others skilled in the art may appreciate and understand the principles and practices of the present disclosure.

The following embodiments and the accompanying drawings, which are incorporated into and form part of this disclosure, illustrate embodiments of the invention and together with the description, serve to explain the principles of the invention. To the accomplishment of the foregoing and related ends, certain illustrative aspects of the invention are described herein in connection with the following description and the annexed drawings. These aspects are indicative, however, of but a few of the various ways in which the principles of the invention can be employed and the subject invention is intended to include all such aspects and their equivalents. Other advantages and novel features of the invention will become apparent from the following detailed description of the invention when considered in conjunction with the drawings.

Figure 1:
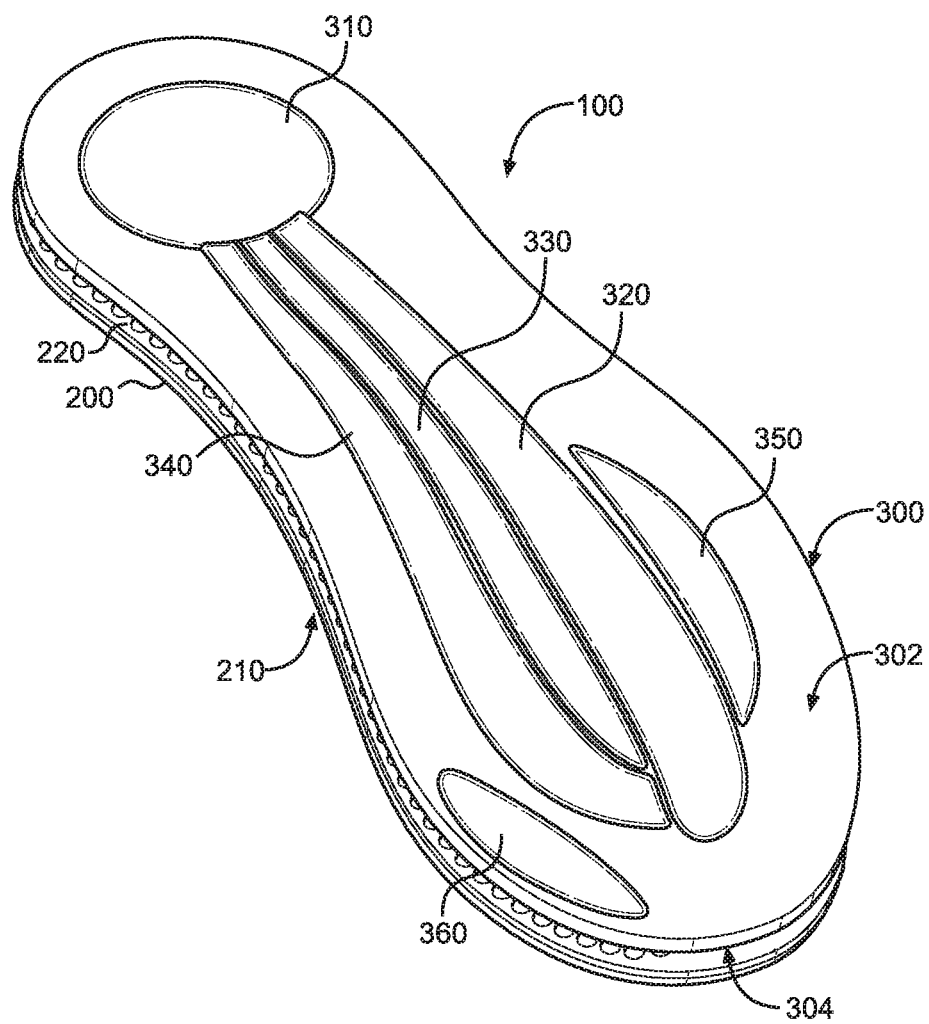
FIG. 1 shows a perspective view of the foot pain relief device including a plurality of detachable sections according to the preferred embodiment of the present invention.
Figure 2:
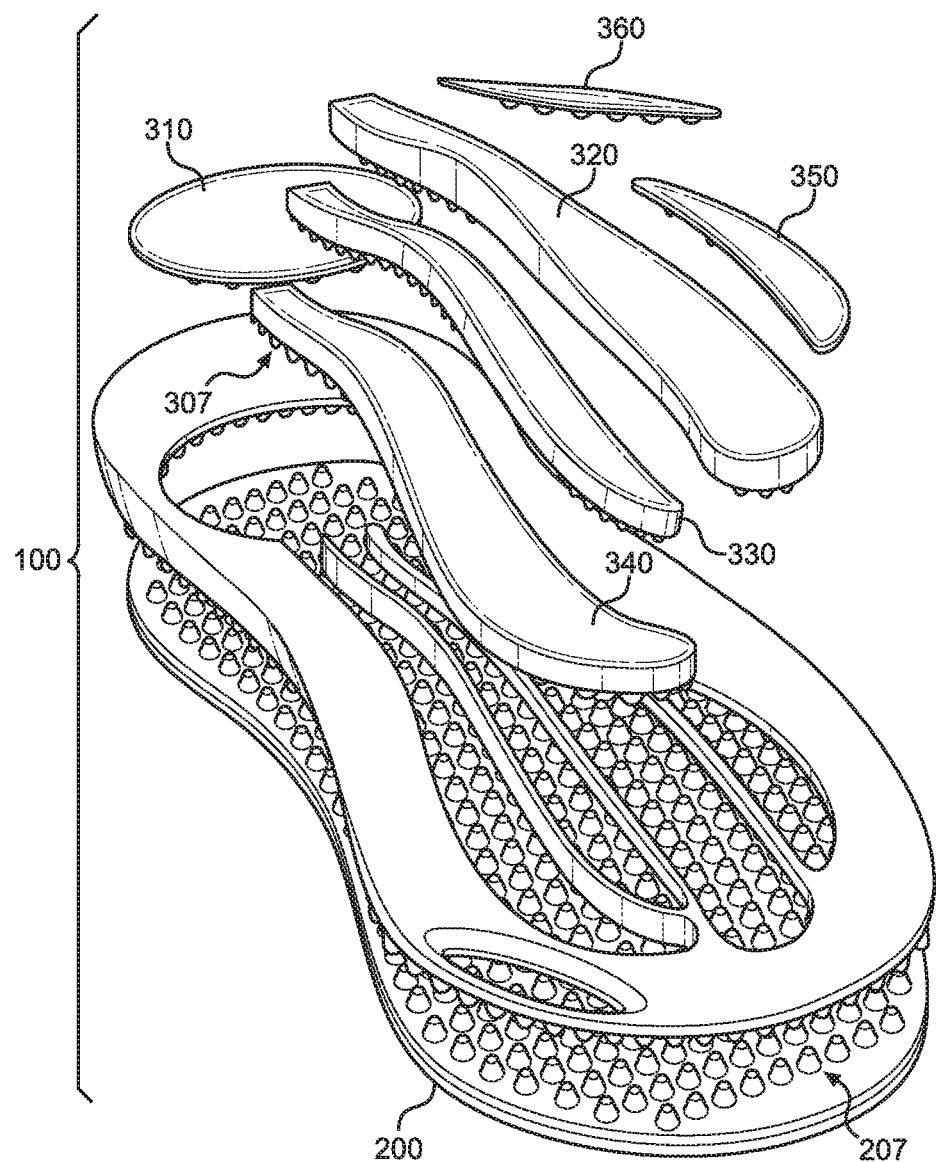
FIG. 2 shows an exploded perspective view of the foot pain relief device according to the preferred embodiment of the present invention of FIG. 1.
Figure 3:
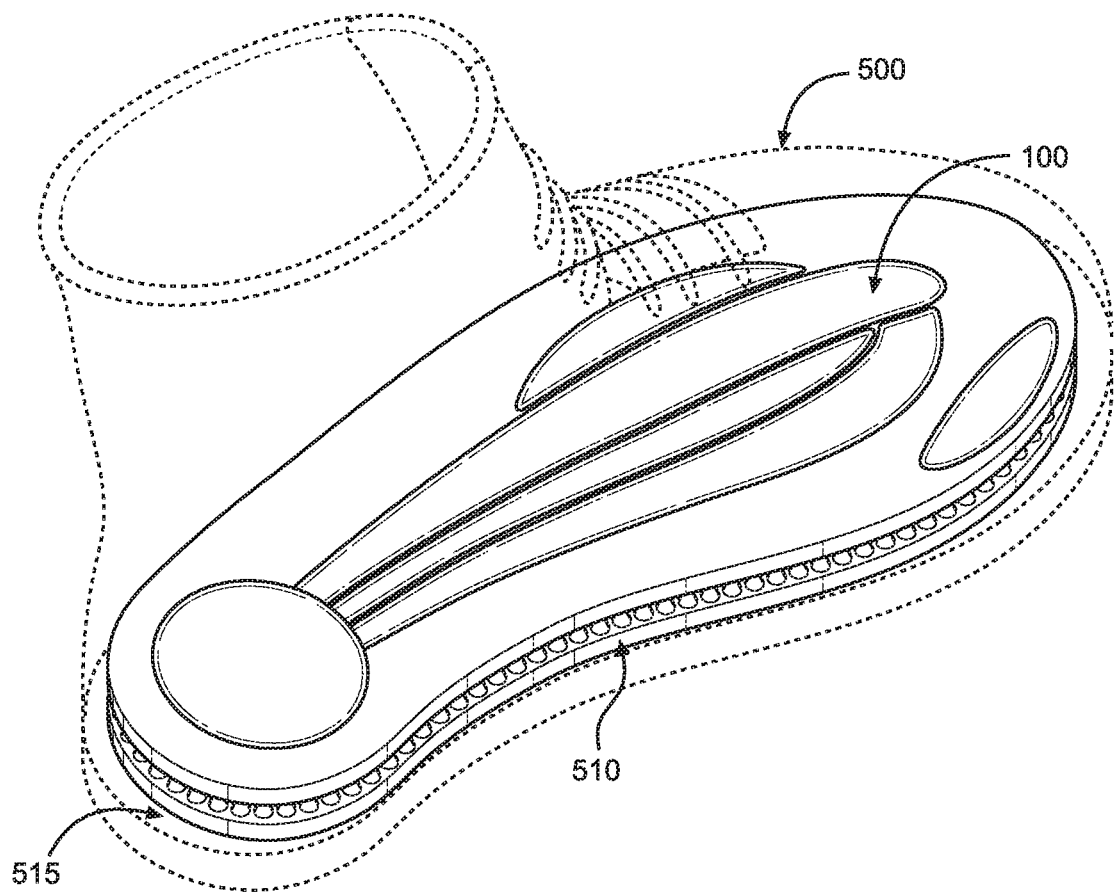
FIG. 3 shows a perspective view of the foot pain relief device according to the preferred embodiment of the present invention of FIG. 1 and placed within footwear.

Turning now descriptively to FIGS. 1-3, the present invention discloses a foot pain relief device 100 comprising a bottom layer 200 including a bottom surface 210, a top surface 220, and a thickness, wherein the bottom layer is formed having a cross-sectional shape adapted to fit within footwear 500 and be securely placed upon a top surface 515 of an inner sole 510 of the footwear; and wherein the bottom layer is formed from a material adapted to releasably hold sections of a top layer thereto; and a top layer 300 having a bottom surface, a top surface, and a thickness, and comprises a plurality of removable sections including a heel section 310, a main plantar muscle section 320, an inner lateral plantar muscle section 330, an outer lateral plantar muscle section 340, a medial plantar muscle section 350 and a toe section 360, wherein the top layer 300 is formed having a cross-sectional shape substantially equal to the cross-sectional shape of the bottom layer 200, wherein the top layer is placed upon the top surface of the bottom layer and is releasably held by the bottom layer thereto, such that each of the plurality of removable sections can be selectively removed from the foot pain relief device to thereby create a hollow portion that allows an injured area of a user's foot to be free from impact during its healing process and while the user continues daily activities without feeling discomfort or pain from the injured area of their foot. And, wherein the bottom layer 200 can be formed from rubber, plastic, nylon, gel, or silicone. And, wherein the top layer 300 can be formed from rubber, plastic, nylon, gel, silicone, leather, and wood. And, wherein the cross-sectional shape of the top layer and the bottom layer is adapted such that the foot pain relief device 100 can fit snugly within footwear 500, be securely placed upon the top surface 515 of the inner sole 510 of the footwear, and cover a substantial portion of the inner sole 510 of the footwear. And, wherein the bottom layer 200 can be formed from a rigid material, and the top layer 300 can be formed from a compressible material. And, wherein the top layer 300 is formed from a lower panel 304 and an upper panel 302, wherein the lower panel 304 is adapted to releasably attach to the top surface 220 of the bottom layer 200, and wherein the upper panel 302 is connected to the lower panel 304 and formed from a material adapted to retain moisture from a user's foot. And, wherein the material of the upper panel 302 is further adapted to reduce odors, and maybe include a carbon material.

In the preferred embodiment, the top surface of the bottom layer 200 includes a plurality of spaced protrusions 207 thereon; wherein the bottom surface of the top layer 300 includes a plurality of spaced protrusions 307 thereon; and wherein the plurality of spaced protrusions of the bottom layer are adapted top interdigitate with the plurality of spaced protrusions of the top layer to thereby prevent movement between the top layer and the bottom layer. And, wherein the plurality of spaced protrusions of the bottom layer and the plurality of spaced protrusions of the top layer can be formed having a shape resembling a cone, a tube, a hemi-spherical bump, or a cube.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention.

Although the invention has been explained in relation to its preferred embodiment, it is to be understood that many other possible modifications and variations can be made without departing from the spirit and scope of the invention.

What is claimed is:

1. A foot pain relief device comprising:
    a bottom layer including:
        a bottom surface;
        a top surface; and
        a thickness;
        wherein said bottom layer is formed having a cross-sectional shape adapted to fit within footwear and be securely placed upon a top surface of an inner sole of said footwear; and
        wherein said bottom layer is formed from a material and in a shape adapted to releasably hold sections of a top layer thereto; and
    a top layer comprising:
        a bottom surface;
        a top surface;
        a thickness;
        a solid outer perimeter;
            wherein said solid outer perimeter extends around the entire circumference of said top layer; and
        a plurality of removable sections comprising:
            a heel section having a round shape;
            a toe section having an oval shape;
            a main plantar muscle section having an elongated and curved shape continuously extending from said heel section and adjacent to said toe section;
            an inner lateral plantar muscle section having an elongated and curved shape continuously extending from said heel section and adjacent to said toe section that is adapted to be placed adjacent to a substantial portion of a first side of said main plantar muscle section;
            an outer lateral plantar muscle section having an elongated and curved shape continuously extending from said heel section and adjacent to said toe section that is adapted to be placed adjacent to a substantial portion of a side of said inner lateral plantar muscle section that is opposite from said side of said inner lateral plantar muscle section adjacent to said main plantar muscle section; and
            a medial plantar muscle section having an elongated and curved shape that is adapted to be placed adjacent to a second side of said main plantar muscle section that is opposite from said first side of said main plantar muscle section that is adjacent to said inner lateral plantar muscle section; and
        wherein said heel section, said main plantar muscle section, said inner lateral plantar muscle section, said outer lateral plantar muscle section, said medial plantar muscle section, and said toe section are located within and spaced from said solid outer perimeter;
        wherein said top layer is formed having a cross-sectional shape substantially equal to said cross-sectional shape of said bottom layer; and
        wherein said top layer is formed from a material and in a shape adapted to be releasably held by said bottom layer;
        wherein said top layer is placed upon said top surface of said bottom layer and is releasably held by said bottom layer thereto, such that each of said plurality of removable sections can be selectively removed from said foot pain relief device to thereby create a hollow portion that allows an injured area of a user's foot to be free from impact during its healing process and while the user continues daily activities without feeling discomfort or pain from the injured area of their foot.

2. The foot pain relief device of claim 1, wherein said bottom layer is formed from a material chosen from a list of materials consisting of rubber, plastic, nylon, gel, and silicone.

3. The foot pain relief device of claim 1, wherein said top layer is formed from a material chosen from a list of materials consisting of rubber, plastic, nylon, gel, silicone, leather, and wood.

4. The foot pain relief device of claim 1, wherein said cross-sectional shape of said top layer and said bottom layer is adapted such that said foot pain relief device can fit snugly within footwear, be securely placed upon a top surface of an inner sole of said footwear, and cover a substantial portion of said inner sole of said footwear.

5. The foot pain relief device of claim 1, wherein said bottom layer is formed from a rigid material; and wherein said top layer is formed from a compressible material.

6. The foot pain relief device of claim 1, wherein said top layer is formed from a lower panel and an upper panel; wherein said lower panel is adapted to releasably attach to said top surface of said bottom layer; and said upper panel is connected to said lower panel and formed from a material adapted to retain moisture from a user's foot.

7. The foot pain relief device of claim 1, wherein said material of said upper panel is further adapted to reduce odors.

8. The foot pain relief device of claim 1, wherein said top surface of said bottom layer includes a plurality of spaced protrusions thereon; wherein said bottom surface of said top layer includes a plurality of spaced protrusions thereon; and wherein said plurality of spaced protrusions of said bottom layer are adapted top interdigitate with said plurality of spaced protrusions of said top layer to thereby prevent movement between said top layer and said bottom layer.

9. The foot pain relief device of claim 8, wherein said plurality of spaced protrusions of said bottom layer and said plurality of spaced protrusions of said top layer are formed having a cone shape.

* * * * *